(12) United States Patent
Kanazawa et al.

(10) Patent No.: US 12,336,776 B2
(45) Date of Patent: Jun. 24, 2025

(54) SURGICAL ROBOT

(71) Applicant: RIVERFIELD INC., Tokyo (JP)

(72) Inventors: Masao Kanazawa, Tokyo (JP); Yasushi Tanaka, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 344 days.

(21) Appl. No.: 17/884,993

(22) Filed: Aug. 10, 2022

(65) Prior Publication Data

US 2022/0378530 A1 Dec. 1, 2022

Related U.S. Application Data

(63) Continuation of application No. PCT/JP2021/000899, filed on Jan. 13, 2021.

(30) Foreign Application Priority Data

Feb. 12, 2020 (JP) ................................ 2020-021630

(51) Int. Cl.
*A61B 34/30* (2016.01)
*A61B 1/00* (2006.01)

(52) U.S. Cl.
CPC ............ *A61B 34/30* (2016.02); *A61B 1/0005* (2013.01); *A61B 2034/301* (2016.02)

(58) Field of Classification Search
CPC . A61B 34/30; A61B 1/0005; A61B 2034/301; A61B 1/00006; A61B 1/00149; A61B 2034/302; A61B 34/37; A61B 90/361; A61B 2090/371

See application file for complete search history.

(56) References Cited

U.S. PATENT DOCUMENTS

| 2002/0055795 | A1* | 5/2002 | Niemeyer | .............. B25J 19/023 |
| | | | | 348/E13.016 |
| 2002/0147384 | A1* | 10/2002 | Uchikubo | ............ A61B 1/0005 |
| | | | | 600/109 |
| 2005/0057496 | A1 | 3/2005 | Uchikubo | |
| 2005/0187432 | A1 | 8/2005 | Hale et al. | |

(Continued)

FOREIGN PATENT DOCUMENTS

| EP | 2 805 669 A1 | 11/2014 | |
| EP | 2925250 B1 * | 7/2017 | ............. A61B 34/30 |

(Continued)

OTHER PUBLICATIONS

JP-2008018257-A translation (Year: 2008).*

(Continued)

*Primary Examiner* — Kyle T Johnson
(74) *Attorney, Agent, or Firm* — Sughrue Mion, PLLC

(57) ABSTRACT

A surgical robot for use in endoscopic surgery includes a control device that implements a position information calculator that calculates information relating to a distal end position of the treatment instrument used in endoscopic surgery, and information relating to a distal end position of an endoscope, a first display section that displays a relative positional relationship between the distal end of the treatment instrument and the distal end of the endoscope by using a calculation result obtained from the position information calculator, and a second display section that displays an image captured by the endoscope.

18 Claims, 6 Drawing Sheets

(56) References Cited

U.S. PATENT DOCUMENTS

| | | | |
|---|---|---|---|
| 2007/0021738 A1* | 1/2007 | Hasser | A61B 34/37 606/1 |
| 2007/0138992 A1* | 6/2007 | Prisco | A61B 34/70 318/568.21 |
| 2009/0171371 A1* | 7/2009 | Nixon | A61B 34/37 700/264 |
| 2009/0326553 A1* | 12/2009 | Mustufa | A61B 34/74 606/130 |
| 2010/0228264 A1* | 9/2010 | Robinson | A61B 18/1206 606/130 |
| 2014/0221748 A1* | 8/2014 | Kikuchi | G02B 23/2484 600/111 |
| 2015/0077528 A1* | 3/2015 | Awdeh | G06F 3/011 348/78 |
| 2015/0272694 A1* | 10/2015 | Charles | G16H 40/63 600/202 |
| 2016/0360120 A1* | 12/2016 | Inoue | A61B 1/00071 |
| 2017/0105608 A1* | 4/2017 | Kura | G02B 23/2484 |
| 2017/0128041 A1 | 5/2017 | Hasser et al. | |
| 2017/0128144 A1 | 5/2017 | Hasser et al. | |
| 2017/0128145 A1 | 5/2017 | Hasser et al. | |
| 2018/0228343 A1* | 8/2018 | Seeber | A61B 34/20 |
| 2019/0090969 A1* | 3/2019 | Jarc | G16H 50/50 |
| 2019/0209262 A1 | 7/2019 | Mustufa et al. | |
| 2019/0388175 A1* | 12/2019 | Tatsuta | A61B 1/06 |
| 2020/0163732 A1 | 5/2020 | Hasser et al. | |
| 2021/0030257 A1* | 2/2021 | Ishihara | A61B 1/00149 |
| 2021/0212790 A1* | 7/2021 | Yoshimura | A61B 5/065 |
| 2021/0330409 A1* | 10/2021 | Kitatsuji | A61B 34/37 |
| 2022/0151721 A1* | 5/2022 | Haraguchi | A61B 34/30 |
| 2022/0160447 A1* | 5/2022 | Haraguchi | A61B 34/30 |
| 2022/0378530 A1* | 12/2022 | Kanazawa | A61B 1/00006 |
| 2023/0125742 A1* | 4/2023 | Kagawa | A61B 90/36 600/104 |
| 2023/0255452 A1* | 8/2023 | Morikawa | A61B 1/00006 600/118 |

FOREIGN PATENT DOCUMENTS

| | | |
|---|---|---|
| EP | 3 351 203 A1 | 7/2018 |
| EP | 3636194 A1 | 4/2020 |
| JP | 2002-306509 A | 10/2002 |
| JP | 2008018257 A * | 1/2008 |
| JP | 2011-525845 A | 9/2011 |
| JP | 4999012 B2 | 8/2012 |
| WO | 2016/069661 A1 | 5/2016 |
| WO | WO-2023238891 A1 * | 12/2023 ............. A61B 34/37 |

OTHER PUBLICATIONS

WO-2023238891-A1 translation (Year: 2023).*
Written Opinion of the International Searching Authority dated Mar. 23, 2021 in International Application No. PCT/JP2021/000899.
International Preliminary Report on Patentability dated Aug. 11, 2022 in International Application No. PCT/JP2021/000899.
Notice of Reasons for Refusal of Japanese Application No. 2020-021630 dated Jun. 30, 2020.
International Search Report of PCT/JP2021/000899 dated Mar. 23, 2021 [PCT/ISA/210].

\* cited by examiner

SURGICAL ROBOT

CROSS-REFERENCE TO RELATED APPLICATIONS

This U.S. Application is a continuation of International Application No. PCT/JP2021/000899, filed Jan. 13, 2021, which is based on and claims priority from Japanese Patent Application No. 2020-021630 filed on Feb. 12, 2020 with the Japan Patent Office, the contents of each of which being herein incorporated by reference in their entireties.

BACKGROUND

The present disclosure relates to a surgical robot for use in endoscopic surgery.

During endoscopic surgery, an operator such as a doctor performs surgery with a treatment instrument while looking at the image captured by the endoscope. If a distal end position of the treatment instrument deviates from an imaging region of the endoscope, the operator will lose sight of the treatment instrument and the surgery will be delayed.

SUMMARY

It is an aspect to provide a surgical robot that allows the operator to easily handle a situation in which the distal end position of the treatment instrument deviates from the imaging region.

According to an aspect of one or more embodiments, there is provided a surgical robot comprising: a control device configured to implement at least one of: a position information calculator that calculates information relating to a distal end position of a treatment instrument used in endoscopic surgery, and information relating to a distal end position of an endoscope; a first display section that displays a relative positional relationship between the distal end of the treatment instrument and the distal end of the endoscope by using a calculation result obtained from the position information calculator; and a second display section that displays an image captured by the endoscope.

According to another aspect of one or more embodiments, there is provided a surgical robot comprising: at least one processor, the at least one processor configured to: calculate information relating to a distal end position of a treatment instrument, a distal end position of an endoscope, and a pivot point position, the pivot point position being a position around which the treatment instrument pivots; display, on a first monitor, first state information and second state information by using a calculation result obtained from the position information calculator; and display, on a second monitor, an image captured by the endoscope, wherein, the first state information comprises a relative positional relationship between the end position of the treatment instrument and the pivot point, and the second state information comprises a relative positional relationship between the distal end of the treatment instrument and the distal end of the endoscope.

According to yet another aspect of one or more embodiments, there is provided a surgical robot comprising: at least one processor, the at least one processor configured to: calculate information relating to a distal end position of a treatment instrument used in endoscopic surgery, and information relating to a distal end position of an endoscope; display, on a first display section, a relative positional relationship between the distal end of the treatment instrument and the distal end of the endoscope based on a result of the calculation; and display, on a second display section, an image captured by the endoscope.

BRIEF DESCRIPTION OF THE DRAWINGS

The above and/or other aspects will become apparent and more readily appreciated from the following description of various embodiments, taken in conjunction with the accompanying drawings of which.

DETAILED DESCRIPTION

Figure 1:
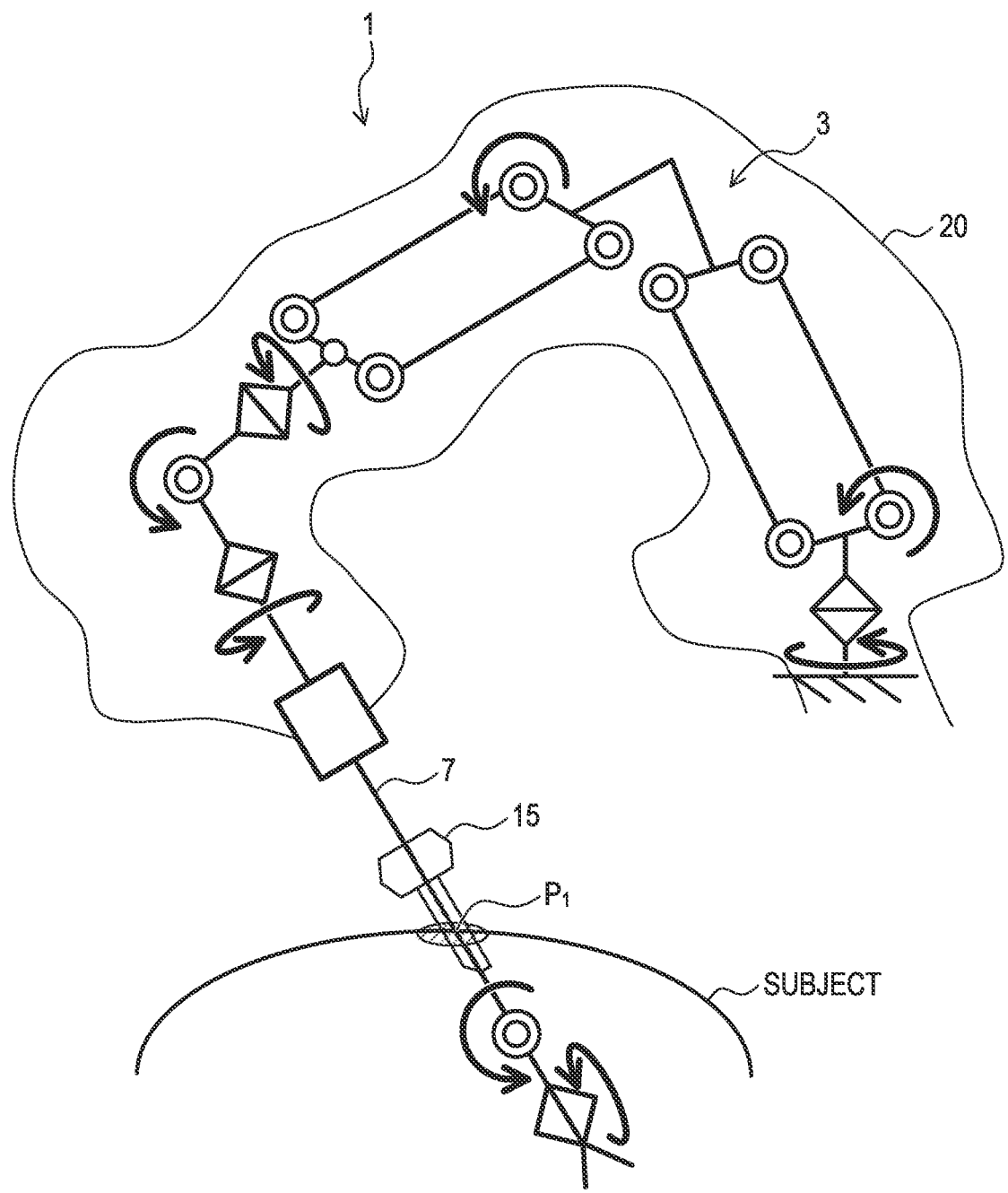
FIG. 1 is an external view of a surgical robot according to some embodiments.

Endoscopic surgery such as laparoscopic surgery is performed by the following procedure.

Specifically, an operator such as a doctor makes two or more small holes in a subject, and inserts a cylindrical trocar into each of the holes.

Next, the operator inserts an endoscope, forceps, an electric scalpel or the like to each trocar, and performs surgery while looking at an image captured by the endoscope. Forceps are an instrument for gripping and pulling an internal organ or the like, and may be remotely controlled. Hereinafter, an instrument, such as forceps and an electric scalpel, for use in treatments performed during surgery is referred to as a treatment instrument.

Thus, in the surgical robot, it is necessary for the operator to be able to easily handle a situation in which the distal end position of the treatment instrument deviates from the imaging region.

In view of the above, the present disclose discloses an example of a surgical robot that allows an operator to operate the treatment instrument even if the distal end position of the treatment instrument deviates from the imaging region.

According to some embodiments, a surgical robot for use in endoscopic surgery may comprise at least the following components: a position information calculator that calculates information relating to a distal end position of a treatment instrument used in endoscopic surgery, and information relating to a distal end position of an endoscope; a first display section that displays a relative positional relationship between the distal end of the treatment instrument and the distal end of the endoscope by using a calculation result obtained from the position information calculator; and a second display section that displays an image captured by the endoscope.

Various embodiments will be described hereinafter.

Arrows indicating directions, hatched lines, etc. shown in the drawings are provided for easy understanding of relationships between the drawings, shapes of members or portions, and others. Accordingly, configurations of a surgical robot, etc. shown in the present disclosure are not limited by the directions shown in the drawings. The drawings with hatched lines do not necessarily show cross-sectional views.

For at least a member or portion described with a reference numeral affixed thereto, there is at least one in number unless specified as "one" or the like. In other words, the member or portion may be two or more in number unless specified as "one". The surgical robot shown in the present disclosure comprises at least components such as members or portions described with reference numerals affixed thereto, and structural portions shown in the drawings.

<1. Configuration of Surgical Robot>

Figure 2:
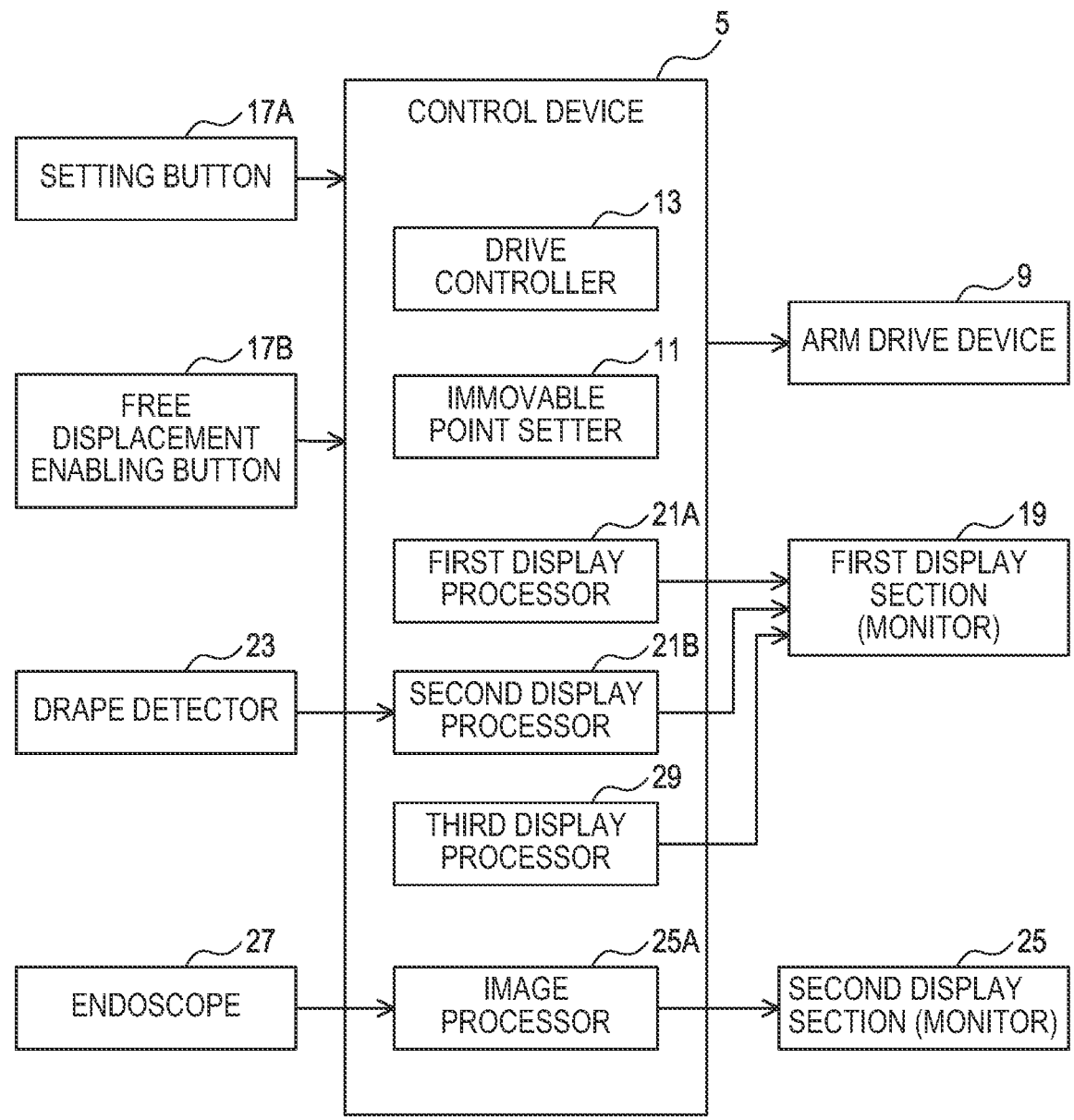
FIG. 2 is a block diagram of the surgical robot according to some embodiments.

FIG. 1 is an external view of a surgical robot according to some embodiments and FIG. 2 is a block diagram of the surgical robot according to some embodiments.

A surgical robot for use in endoscopic surgery will be described with reference to FIGS. 1 and 2.

As shown in FIG. 2, a surgical robot 1 may comprise a control device 5, an arm drive device 9, a first display section 19 and a second display section 25, in addition to a robot arm 3 (see FIG. 1).

<Robot Arm>

The robot arm 3 is an example of an arm device holding a treatment instrument 7, as shown in FIG. 1. Specifically, the robot arm 3 is configured by a link mechanism that has two or more joints and that may change a position of pivot.

The pivot is a position which is an immovable point when the robot arm 3 operates, regardless of a state of the robot arm 3. The treatment instrument 7 is an instrument, such as forceps and an electric scalpel, used in treatments performed during surgery.

The treatment instrument 7 shown in FIG. 1 is a forceps, by way of example. At a distal end of the forceps, a hand part for gripping and pulling an internal organ or the like is provided. The robot arm 3 is covered by a drape 20. In some embodiments, the drape 20 may be tubular. The drape 20 may be a flexible, non-woven fabric covering member.

An endoscope 27 (see FIG. 2) may be gripped by a second robot arm. Hereinafter, the treatment instrument 7 and the endoscope 27 are collectively called surgical instrument. In other words, the surgical instrument is an instrument used for endoscopic surgery, such as an endoscope, forceps and an electric scalpel.

<Arm Drive Device>

The arm drive device 9 is an example of a drive device that drives the robot arm 3. The arm drive device 9 according some embodiment may comprise two or more electric motors, an air pressure cylinder, and a pressure generator.

Each electric motor drives a corresponding joint. The air pressure cylinder applies tension to a wire that drives the treatment instrument 7 (for example, hand part of the forceps). The pressure generator supplies a compressed air to the air pressure cylinder.

The second robot arm is driven by a second arm drive device. The second arm drive device may have the same configuration as that of the arm drive device 9 and operation of the second arm drive device may be controlled in the same manner as that of the arm drive device 9.

<Control Device>

The control device 5 comprises at least an immovable point setter 11, a drive controller 13, a first display processor 21A, a second display processor 21B, a third display processor 29 and an image processor 25A, as shown in FIG. 2. The control device 5 may be implemented by one or more microprocessors or by hardware control logic.

The immovable point setter 11 recognizes a position of a site where a trocar 15 (see FIG. 1) is inserted during surgery (hereinafter, also referred to as an incision position), and stores the recognized position as a pivot $P_1$.

Hereinafter, a series of operations from recognition of the incision position to storage of the position, etc. by the immovable point setter 11 is referred to as immovable point setting. A state in which the immovable point setting may be performed is referred to as an immovable point setting mode.

The trocar 15 is a cylindrical member to be inserted into a hole incised in a subject. In other words, a surgical instrument like the treatment instrument 7, such as forceps, and the endoscope 27 is inserted into a body of the subject through the trocar 15 inserted to an incision site.

<Drive controller>

The drive controller 13 uses the position of the pivot $P_1$ to control operation of the arm drive device 9. Specifically, the drive controller 13 receives a command signal outputted from a master-side input operation device, and activates the arm drive device 9 according to the command signal.

At this time, the drive controller 13 activates the arm drive device 9 so that a portion of the treatment instrument 7 corresponding to the pivot $P_1$ is immovable. The mater-side input operation device is an example of an input device which is directly operated by an operator such as a doctor.

Operation of the second arm drive device is controlled by a second drive controller. The second drive controller activates the second robot arm with the incision site where the endoscope 27 is to be inserted as the pivot $P_1$.

The pivot is an immovable point set by a second immovable point setter. The second immovable point setter is identical to the immovable point setter 11, and thus a detailed description of the second immovable point setter is omitted herein.

The surgical robot according to some embodiments uses the input operation device for the robot arm 3 (in other words, arm drive device 9) to transmit the command signal to the second arm drive device. Specifically, the surgical robot is provided with a selector switch.

The selector switch may switch an output destination of the aforementioned command signal between the arm drive device 9 and the second arm drive device. The operator may operate the selector switch to switch between activation of the robot arm 3 and activation of the second robot arm.

<2. Detail of Immovable Point Setter>

The immovable point setter 11 according to some embodiments may execute a position recognition function and a memory function. The immovable point setter 11 uses the position recognition function and the memory function to store the position of the pivot $P_1$ as an immovable point.

The position recognition function is a function to recognize a distal end position of the treatment instrument 7 held by the robot arm 3. The memory function stores the distal end position recognized by the position recognition function as the pivot $P_1$. The pivot $P_1$ stored by the memory function may be, for example, a position recognized by the position recognition function. Also, the position recognized by the position recognition function is not limited to the distal end position of the treatment instrument 7. The position recognized by the position recognition function may be, for example, the incision position which is the position of a site where the trocar 15 is to be inserted during surgery.

The position recognition function according to some embodiments recognizes the distal end position of the treatment instrument 7 by obtaining or calculating a coordinate or the like which indicates the distal end position of the treatment instrument 7 from an attitude of the robot arm 3. The memory function stores the coordinate as the pivot $P_1$.

To perform the immovable point setting, a surgical instrument equivalent may be used instead of the treatment instrument 7. The surgical instrument equivalent is a member having a shape similar to that of the treatment instrument 7. Specifically, for example, in some embodiments a rod-shaped or pipe-shaped member may correspond to the surgical instrument equivalent. In case of the second immovable point setter, the endoscope 27 corresponds to the surgical instrument equivalent.

The position recognition function and memory function according to some embodiments are implemented by a software, programs that make up the software, and a microcomputer. The microcomputer at least comprises a CPU, a ROM and a RAM to run the software. The software is stored in a non-volatile storage section in advance.

The surgical robot 1 has a setting button 17A, a free displacement enabling button 17B and the like, as shown in FIG. 2. The setting button 17A and the free displacement enabling button 17B are provided in at least one of the robot arm 3 and the control device 5. The robot arm 3 corresponds to an example of a slave device, and the control device 5 corresponds to an example of a master-side device.

The setting button 17A is an example of a setting operating section operated by a user. The user is the one who performs an immovable point setting work. Specifically, the user is an operator such as a doctor or those who assist surgery. When the setting button 17A is operated, an immovable point setting mode starts or ends.

In other words, if the setting button 17A is operated in a mode other than the immovable point setting mode, the immovable point setting mode is started. If the setting button 17A is operated in the immovable point setting mode, the immovable point setting mode ends.

Specifically, if the setting button 17A is depressed for more than a specified time (for example, three seconds), the immovable point setting mode is started. When the immovable point setting mode is started, the position recognition function is enabled.

When the setting button 17A is depressed less than the specified time (for example, two seconds), the position recognition function is executed and then the memory function is executed. Thereafter, the pivot $P_1$ is stored as the immovable point, and the immovable point setting mode ends.

The free displacement enabling button 17B is an example of the operating section operated by the user. When the free displacement enabling button 17B is operated, the arm drive device 9 is brought into a free displacement mode. The free displacement mode is a mode in which the robot arm 3 is freely displaceable in accordance with an external force acting on the robot arm 3.

Therefore, in the free displacement mode, the user may freely displace the robot arm 3 by pushing and pulling the robot arm 3. In other words, in the free displacement mode, the user may align the distal end of the treatment instrument 7 with the incision position by pushing and pulling the robot arm 3 without operating the master-side input operation device.

The free displacement mode ends if the free displacement enabling button 17B is operated in the free displacement mode, or when the immovable point setting mode ends. In a state in which the free displacement mode is not started, the robot arm 3 is not displaced even if an external force acts on the robot arm 3.

<Control in Immovable Point Setting Mode>

Figure 3:
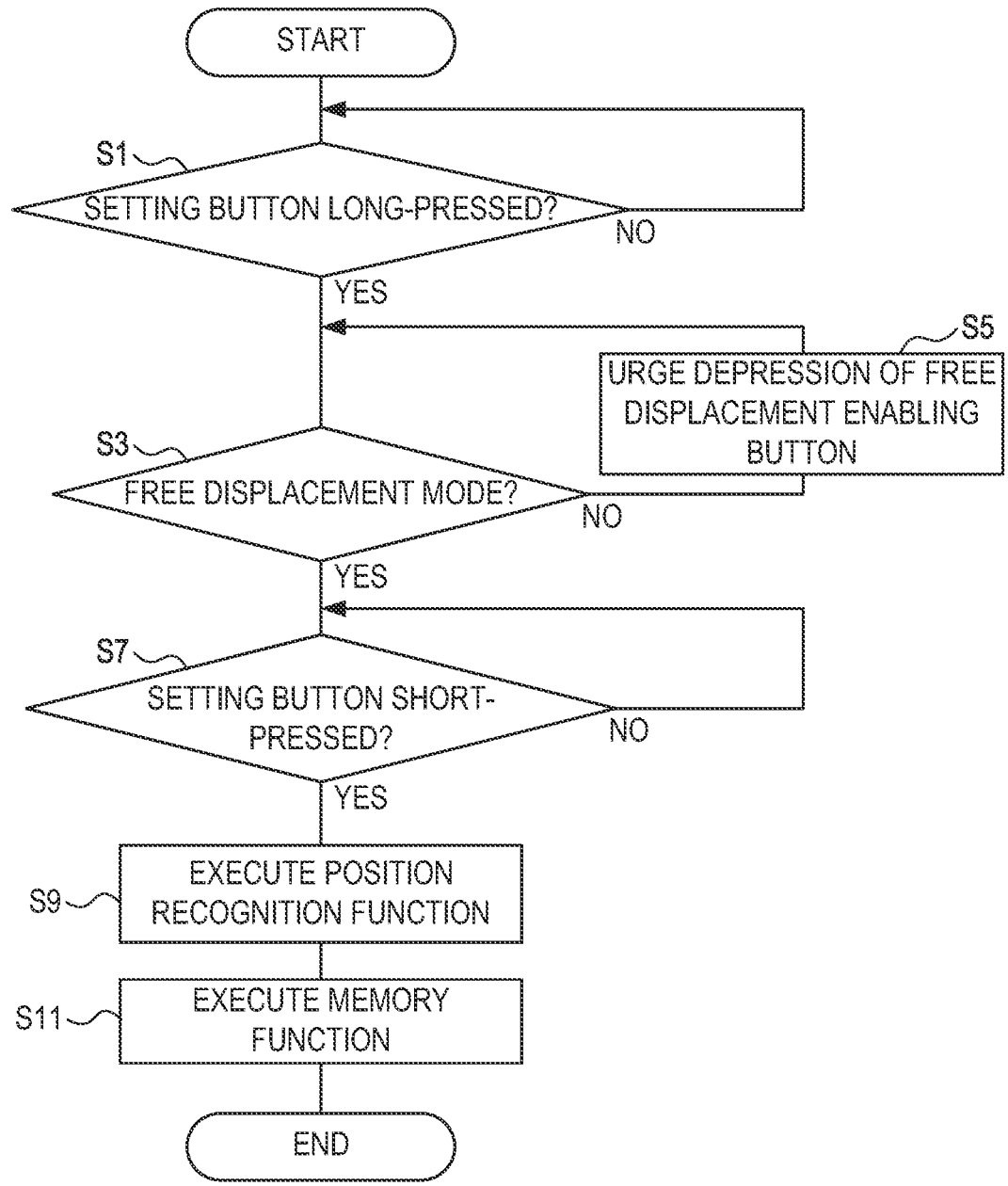
FIG. 3 is a flowchart showing a control of an immovable point setting mode of the surgical robot according to some embodiments.

FIG. 3 is a flowchart showing a control of an immovable point setting mode of the surgical robot according to some embodiments. FIG. 3 shows an example control of the control device 5 executed in the immovable point setting mode. The control device 5 determines whether the setting button 17A is depressed for more than a specified time (for example, three seconds) (S1). "(S1)" and the like indicate control step numbers illustrated in FIG. 3.

The control device 5, when determining that the setting button 17A is not depressed for more than the specified time (S1: NO), continues to monitor whether the setting button 17A is depressed, i.e., the process returns to S1. The control device 5, when determining that the setting button 17A is depressed for more than the specified time (S1: YES), determines whether the arm drive device 9 is in the free displacement mode (S3).

The control device 5, when determining that the arm drive device 9 is not in the free displacement mode (S3: NO), urges the user to operate the free displacement enabling button 17B by sound (for example, buzzer) or by a notification device such as a warning light (S5).

The control device 5, when determining that the arm drive device 9 is in the free displacement mode (S3: YES), determines whether the setting button 17A is depressed for less than the specified time (for example, two seconds) (S7).

The control device 5, when determining that the setting button 17A is not depressed for less than the specified time (S7: NO), returns to S7. The control device 5, when determining that the setting button 17A is depressed for less than the specified time (S7: YES), executes the position recognition function (S9) to recognize a distal end position of the surgical instrument 7 held by the robot arm 3, and then executes the memory function (S11) to store the distal end position recognized by the position recognition function as the pivot $P_1$.

In other words, some embodiments, when the arm drive device 9 is not in the free displacement mode (S3: NO), the position recognition function and the memory function are virtually disabled.

The control device 5, after storing the pivot $P_1$ as the immovable point, ends the immovable point setting mode and the free displacement mode, and notifies the user that the pivot $P_1$ is stored as the immovable point.

<3. Notification of Information>

The first display section 19 and the second display section 25 shown in FIG. 2 are monitors that transmit information such as text information and image information to the user. On the first display section 19, information relating to the surgical robot 1 (hereinafter, referred to as state information), etc. are displayed. On the second display section 25, an image captured by the endoscope 27 is displayed.

The endoscope 27 according to some embodiments may be configured by a camera such as a stereo camera that may image an object three-dimensionally. The image processor 25A is a processor for displaying a three-dimensional image on the second display section 25.

<Display of First State Information>

The first display processor 21A and the second display processor 21B display information on the first display section 19. The first display processor 21A displays a relative positional relationship between the incision position, that is, the pivot $P_1$ and the distal end position of the treatment instrument 7 on the first display section 19.

The first display processor 21A according to some embodiments uses image information such as figures (for example, icons) to display the relative positional relationship on the display section 19. Each icon has a figure which represents the pivot $P_1$ or the distal end position of the treatment instrument 7.

Figure 4A:
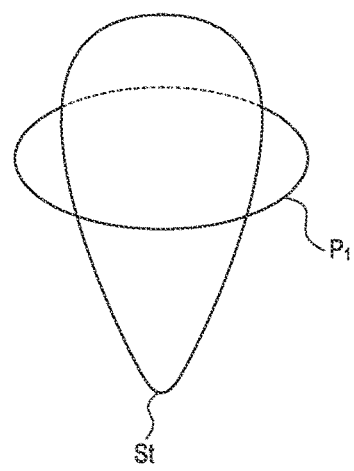
FIGS. 4A, 4B and 4C are diagrams showing display examples of a first state display.
Figure 4B:
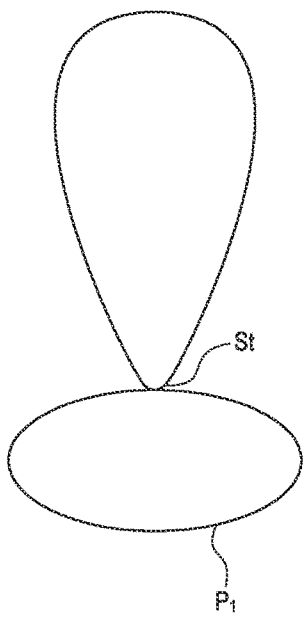
Figure 4C:
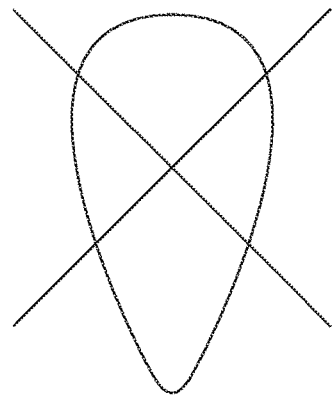

FIGS. 4A to 4C are diagrams showing display examples of a first display state. Specifically, for example, FIG. 4A shows a case where the distal end position St of the treatment instrument 7 is located inside a body relative to the pivot $P_1$. FIG. 4B shows a case where the distal end position St of the treatment instrument 7 is located outside the body relative to the pivot $P_1$. FIG. 4C shows a state in which the immovable point setting is not yet performed.

The second display processor 21B displays a detection result of the drape detector 23 (see FIG. 2) on the first display section 19. The drape detector 23 detects whether the drape 20 is attached to the robot arm 3. The drape detector 23 is provided in the robot arm 3.

Figure 5A:
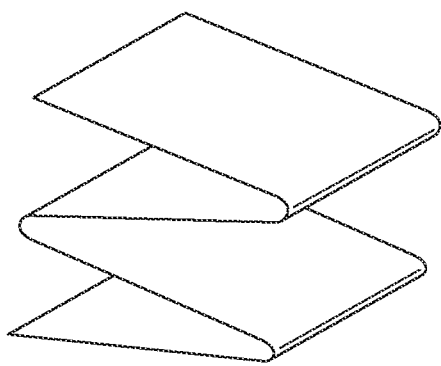
FIGS. 5A and 5B are diagrams showing display examples of the first state display.
Figure 5B:
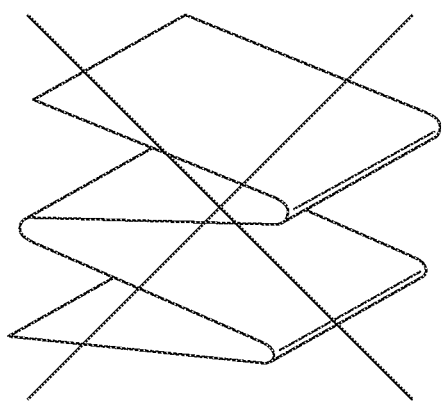

FIGS. 5A and 5B are diagrams showing display examples of the first display state. If the drape 20 is attached to the robot arm 3, the second display processor 21B displays information (for example, see FIG. 5A) indicating that the drape 20 is attached to the robot arm 3 on the display section 19. If the drape 20 is not attached to the robot arm 3, the second display processor 21B displays information (for example, see FIG. 5B) on the display section 19 indicating that the drape 20 is not attached to the robot arm 3.

<Display of Second State Information>

The third display processor 29 displays a relative positional relationship between the distal end position of the treatment instrument 7 and the distal end position of the endoscope 27 on the first display section 19. In other words, the third display processor 29 may perform at least three functions.

Specifically, the first function is a function to obtain information relating to the distal end position of the treatment instrument 7. The second function is a position information calculation function to calculate information relating to the distal end position of the endoscope 27. The third function is a function to display the information relating to the distal end position of the treatment instrument 7 and the information relating to the distal end position of the endoscope 27 on the first display section 19. The third display processor 29 according to some embodiments may use the aforementioned position recognition function to achieve the first function and the second function.

Figure 6:
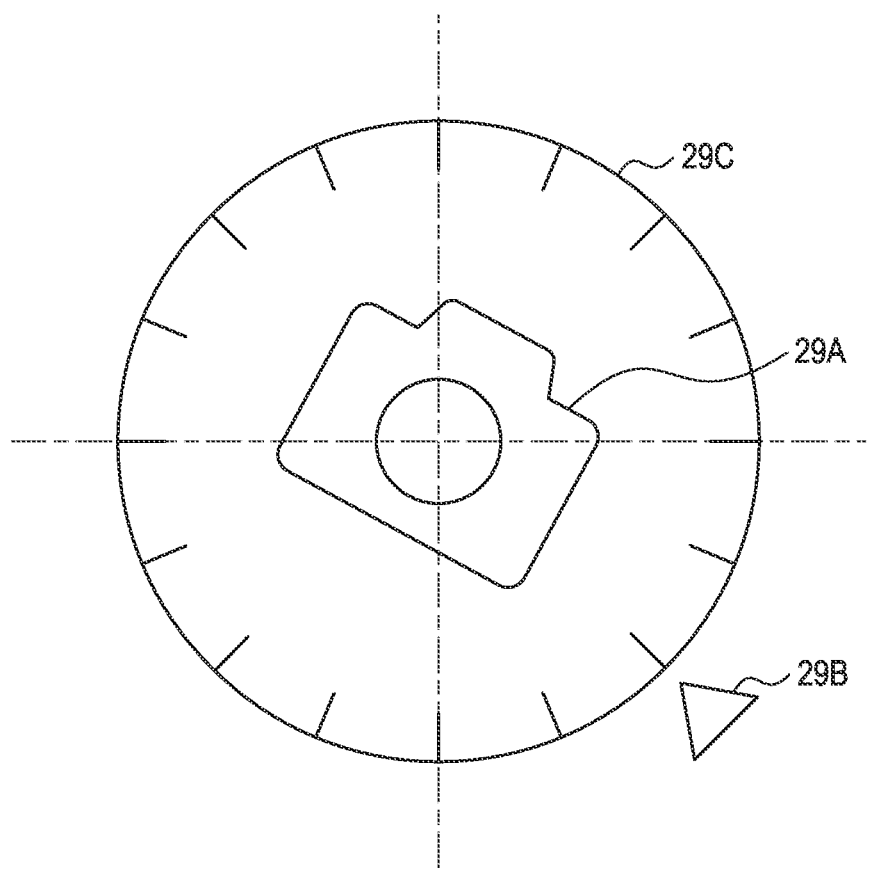
FIG. 6 is a diagram showing a display example of a second state display.

FIG. 6 is a diagram of a display example of a second state display. The third display processor 29 uses a calculation result by the position information calculation function to display the relative positional relationship between the distal end of the treatment instrument 7 and the distal end of the endoscope 27. Specifically, as shown in FIG. 6, a figure (for example, icon) 29B representing the distal end of the treatment instrument 7 and a figure (for example, icon) 29A representing the distal end of the endoscope 27 are at least displayed on the first display section 19.

Further, on the first display section 19, together with the two types of icons 29A and 29B, a circular protractor 29C based on the position of the distal end of the endoscope 27 is displayed. The circular protractor 29C may be displayed in a state in which a center of the circular protractor 29C coincides with a center of the display screen of the first display section 19.

The center of the display screen of the first display section 19 may mean the center of the physical display screen when only the second state information is displayed on the first display section 19, and may mean a center of a display area of the second state information when other information (for example, first state information), in addition to the second state information, is also displayed on the first display section 19.

In the surgical robot 1 according some embodiments, the center of the display area of the second state information coincides with the center of the physical display screen. Therefore, even if two or more types of state information are displayed, the center of the circular protractor 29C coincides with the center of the physical display screen.

The icon (hereinafter, also referred to as a camera icon) 29A representing the distal end of the endoscope 27 is displayed in the center of the display screen. A display mode of the icon 29B representing the treatment instrument 7 or a display position of the icon 29B changes in accordance with changes in the relative positional relationship between the distal end position of the treatment instrument 7 and the distal end position of the endoscope 27.

The display mode of the icon 29B may mean, for example, specific designs of the icon 29B, such as, the shape, pattern, and color of the icon 29B or combinations thereof, or how to display those specific designs (for example, blinking display and always-on display), etc.

An up-down direction of the display screen or the display area coincides with a vertical direction. The display angle of the camera icon 29A relative to the display screen changes in accordance with an angle of rotation of the endoscope 27. In other words, when the endoscope 27 rotates, the camera icon 29A also rotates in conjunction with the rotation of the endoscope 27. A center position of the camera icon 29A always coincides with the center of the display screen (in other words, center of the circular protractor 29C) regardless of the physical position of the endoscope 27.

<4. Features of Surgical Robot According to Some Embodiments>

In the surgical robot 1 according to some embodiments, the relative positional relationship between the distal end of the treatment instrument 7 and the distal end of the endoscope 27 is displayed on the first display section 19. Thus, in the surgical robot 1, the operator may easily deal even with the case where the distal end position of the treatment instrument 7 deviates from the imaging region.

In some embodiments, the monitor to display the state information and the monitor to display the image captured by the endoscope 27 is separately provided. This configuration facilitates surgery by the operator. The monitor to display the state information corresponds to an example of the configuration as the first display section 19, and the monitor to display the image captured by the endoscope 27 corresponds to an example of the configuration as the second display section 25.

If, in addition to the image captured by the endoscope 27 (hereinafter, captured image), the state information is also displayed on the second display section 25, it becomes difficult for the operator to perform surgery since the display of the state information partially hides the captured image.

In some embodiments, together with the positional relationship of the two types of icons 29A and 29B, the circular protractor 29C based on the position of the distal end of the endoscope 27 is displayed on the first display section 19. This allows the operator to easily grasp the distal end position of the treatment instrument 7.

In some embodiments, in a state in which the center of the circular protractor 29C coincides with the center of the display screen of the first display section 19, the icon 29A representing the distal end of the endoscope 27 is displayed in the center of the display screen, and, in accordance with changes in the positional relationship, the display mode of the icon 29B representing the treatment instrument 7 or the display position of the icon 29B changes. This configuration allows the operator to easily grasp the distal end position of the treatment instrument 7.

In some embodiments, the up-down direction of the display screen coincides with the vertical direction. This configuration allows the operator to easily grasp the distal end position of the treatment instrument 7.

In the surgical robot 1 according to some embodiments, the relative positional relationship between the site where the trocar 15 is to be inserted during surgery and the distal end position of the treatment instrument 7 is displayed on the first display section 19. This display of the relative positional relationship allows the operator to confirm whether the treatment instrument 7 is moving so that the portion of the treatment instrument 7 corresponding to the incision site is immovable.

In other words, whether the surgical robot 1 has recognized the site where the trocar 15 is to be inserted as the immovable point, that is, whether surgery by the surgical robot 1 is ready to be performed may be easily and reliably recognized by the operator.

The first display processor 21A uses the position stored by the immovable point setter 11 as the site where the trocar 15 is to be inserted. This configuration allows the operator to easily and reliably recognize whether the immovable point setter 11 stores the incision position as the immovable point.

In the surgical robot 1 according to some embodiments, the detection result of the drape detector 23 is displayed on the first display section 19. This display allows the operator to easily and reliably recognize whether surgery by the surgical robot 1 is ready to be performed.

The surgical robot 1 according to some embodiments recognizes the position of the site where the trocar 15 is to be inserted during surgery, that is, the incision position, and stores the recognized position as the pivot $P_1$. Thus, in the surgical robot 1, alignment work between the position of the pivot $P_1$ and the incision site may be easily performed.

The arm drive device 9 may execute the free displacement mode. Thus, in the surgical robot 1, the user may execute the position recognition function and the memory function after aligning the distal end of the treatment instrument 7 with the incision site. Accordingly, alignment work between the position of the pivot $P_1$ and the incision site may be easily performed.

OTHER EMBODIMENTS

In some embodiments, the robot arm 3 for holding the treatment instrument 7 and the second robot arm for holding the endoscope 27 are provided. However, embodiments are not limited to the configuration provided with the second robot arm.

Specifically, for example, some embodiments may be configured so that there is no second robot arm and the endoscope 27 is held by an assistant or that there are two or more robot arms 3 which hold two or more treatment instruments 7.

In the description of FIGS. 1-6, the circular protractor 29C based on the position of the distal end of the endoscope 27 is displayed on the first display section 19. However, embodiments are not limited to the configuration in which the circular protractor 29C is displayed on the first display section 19. Specifically, for example, some embodiments may be configured so that the circular protractor 29C is not displayed.

In the description with reference to FIGS. 1-6, the up-down direction of the display screen coincides with the vertical direction, and, in accordance with changes in the positional relationship, the display mode of the icon 29B representing the treatment instrument 7 or the display position of the icon 29B changes. However, embodiments are not limited to the configuration in which the up-down direction of the display screen coincides with the vertical direction, and, in accordance with changes in the positional relationship, the display mode of the icon 29B representing the treatment instrument 7 or the display position of the icon 29B changes.

The robot arm 3 described by FIGS. 1-6 is configured by a link mechanism that may change the position of pivot. However, embodiments are not limited to the configuration in which the robot arm 3 is configured by a link mechanism that may change the position of pivot. Specifically, for example, some embodiments the pivot (also referred to as an immovable point) may be immovable relative to the robot body, in other words, unchangeable.

In the description of FIGS. 1-6, the second display processor 21B is provided. However, embodiments are not limited to the configuration in which the second display processor 21B is provided. Specifically, for example, the present disclosure may be configured so that the second display processor 21B is omitted, etc.

In the description of FIGS. 1-6, if the arm drive device 9 is not in the free displacement mode (S7: NO), the control device 5 disables the position recognition function and the memory function. However, embodiments are not limited to the control device 5 which disables the recognition function and the memory function if the arm drive device 9 is not in the free displacement mode.

Specifically, for example, in some embodiments, even in a mode other than the free displacement mode, the position recognition function and the memory function are enabled. In this case, the master-side input operation device may be used to align the distal end of the treatment instrument 7 with the incision position.

The immovable point setter 11 according to FIGS. 1-6 obtains the coordinate representing the distal end position of the treatment instrument 7 from the attitude of the robot arm 3 to recognize the distal end position. However, embodiments are not limited to the configuration in which the immovable point setter 11 obtains the coordinate representing the distal end position of the treatment instrument 7 from the attitude of the robot arm 3 to recognize the distal end position. Specifically, for example, in some embodiments the distal end position may be recognized with an image analysis technique that uses a 3D camera such as a stereo camera and a depth camera.

In the description referenced in FIGS. 1-6, the user recognizes the distal end of the treatment instrument 7 or a surgical instrument equivalent, in a state in which the distal end is aligned with the incision position, to recognize the incision position. However, embodiments are not limited to the configuration in which the user recognizes the distal end of the treatment instrument 7 or a surgical instrument equivalent, in a state in which the distal end is aligned with the incision position, to recognize the incision position. Specifically, for example, in some embodiments a laser light may be applied to the incision position, and the applied position may be recognized by an image analysis technique.

In the description of FIGS. 1-6, when the free displacement enabling button 17B is operated, the free displacement mode is started. However, embodiments are not limited to the configuration in which, when the free displacement enabling button 17B is operated, the free displacement mode is started. Specifically, for example, in some embodiments, at the same time as the immovable point setting mode is started, the free displacement mode may be automatically started.

Various embodiments have been described above with reference to the drawings. However, it is to be understood that the present disclosure is not limited to the above embodiments, but various changes and modifications may be made therein without departing from the spirit and scope thereof as set forth in appended claims.

What is claimed is:

1. A surgical robot comprising:
    a control device that comprises a memory, and a processor that in conjunction with the memory are configured to implement at least:
    a position information calculator that calculates information relating to a distal end position of a treatment instrument used in endoscopic surgery, information relating to a distal end position of an endoscope, and information relating to a pivot point position, the pivot point position being a pivot point around which the treatment instrument pivots;
    a first display section that displays a relative positional relationship between a distal end of the treatment instrument and a distal end of the endoscope and a relative positional relationship between the distal end position of the treatment instrument and the pivot point by using a calculation result obtained from the position information calculator; and
    a second display section that displays an image captured by the endoscope.

2. The surgical robot according to claim 1, wherein a circular protractor based on the distal end position of the endoscope is displayed on the first display section, together with the relative positional relationship between the distal end of the treatment instrument and the distal end of the endoscope.

3. The surgical robot according to claim 2, wherein
    in a state in which a center of the circular protractor coincides with a center of a display screen of the first display section, a figure representing the distal end of the endoscope is displayed in the center of the display screen, and
    a display mode or a display position of a figure representing the treatment instrument changes in accordance with changes in the relative positional relationship between the distal end of the treatment instrument and the distal end of the endoscope.

4. The surgical robot according to claim 3, wherein a vertical direction of the display screen coincides with a vertical movement direction of the treatment instrument.

5. The surgical robot according to claim 4, wherein
    when the figure representing the distal end of the endoscope is a camera icon,
    a display angle of the camera icon relative to the display screen changes in accordance with an angle of rotation of the endoscope.

6. The surgical robot according to claim 3, wherein
    when the figure representing the distal end of the endoscope is a camera icon,
    a display angle of the camera icon relative to the display screen changes in accordance with an angle of rotation of the endoscope.

7. A surgical robot comprising at least one processor configured to at least:
    calculate information relating to a distal end position of a treatment instrument, a distal end position of an endoscope, and a pivot point position, the pivot point position being a pivot point around which the treatment instrument pivots;
    display, on a first monitor, first state information and second state information by using a result of the calculation; and
    display, on a second monitor, an image captured by the endoscope,
    wherein the first state information comprises a relative positional relationship between the distal end position of the treatment instrument and the pivot point, and
    the second state information comprises a relative positional relationship between a distal end of the treatment instrument and a distal end of the endoscope.

8. The surgical robot according to claim 7, wherein the at least one processor is further configured to display a circular protractor based on the position of the distal end of the endoscope on the first monitor.

9. The surgical robot according to claim 8, wherein a center of the circular protractor coincides with a center of a display screen of the first monitor.

10. The surgical robot according to claim 9, wherein:
    when only the second state information is displayed on the first monitor, the center of the display screen is a center of the first monitor; and
    when the first state information and the second state information are displayed on the first monitor, the center of the display screen is a center of a display area of the second state information.

11. The surgical robot according to claim 7, wherein the at least one processor is further configured to display a figure representing the distal end of the endoscope at a center of a display screen of the first monitor.

12. The surgical robot according to claim 11, wherein the at least one processor is configured to change a display position of a figure representing the distal end of the treatment instrument in accordance with changes in the relative positional relationship between the distal end of the treatment instrument and the distal end of the endoscope.

13. A surgical robot comprising at least one processor configured to:
    calculate information relating to a distal end position of a treatment instrument used in endoscopic surgery, information relating to a distal end position of an endoscope, and information relating to a pivot point position, the pivot point position being a pivot point around which the treatment instrument pivots;
    display, on a first display, a relative positional relationship between a distal end of the treatment instrument and a distal end of the endoscope and a relative positional relationship between the distal end position of the treatment instrument and the pivot point based on a result of the calculation; and
    display, on a second display, an image captured by the endoscope.

14. The surgical robot according to claim 13, wherein the at least one processor is further configured to display, on the first display, a circular protractor based on the distal end position of the endoscope.

15. The surgical robot according to claim 14, wherein in a state in which a center of the circular protractor coincides with a center of a display screen of the first display, the at least one processor is configured to display a figure representing the distal end of the endoscope in the center of the display screen, and
    wherein a display mode or a display position of a figure representing the treatment instrument changes in accordance with changes in the relative positional relationship between the distal end of the treatment instrument and the distal end of the endoscope.

16. The surgical robot according to claim 15, wherein a vertical direction of the display screen coincides with a vertical movement direction of the treatment instrument.

17. The surgical robot according to claim 16, wherein, when the figure representing the distal end of the endoscope is a camera icon, the at least one processor is configured to change a display angle of the camera icon relative to the display screen in accordance with an angle of rotation of the endoscope.

18. The surgical robot according to claim 15, wherein, when the figure representing the distal end of the endoscope is a camera icon, the at least one processor is configured to change a display angle of the camera icon relative to the display screen in accordance with an angle of rotation of the endoscope.

* * * * *